(12) United States Patent
Scianamblo

(10) Patent No.: US 7,094,056 B2
(45) Date of Patent: Aug. 22, 2006

(54) ENDODONTIC INSTRUMENT HAVING REVERSED HELIX

(76) Inventor: Michael J. Scianamblo, 1526 Fifth Ave., San Rafael, CA (US) 94901

( * ) Notice: Subject to any disclaimer, the term of this patent is extended or adjusted under 35 U.S.C. 154(b) by 0 days.

(21) Appl. No.: 10/764,337

(22) Filed: Jan. 22, 2004

(65) Prior Publication Data

US 2004/0219484 A1 Nov. 4, 2004

Related U.S. Application Data

(60) Provisional application No. 60/477,688, filed on Jun. 10, 2003, and provisional application No. 60/467,472, filed on May 1, 2003.

(51) Int. Cl.
*A61C 5/02* (2006.01)

(52) U.S. Cl. ...................................................... 433/102
(58) Field of Classification Search ................ 433/102, 433/165, 224
See application file for complete search history.

(56) References Cited

U.S. PATENT DOCUMENTS

| | | | |
|---|---|---|---|
| 4,353,698 A | 10/1982 | McSpadden | |
| 4,457,710 A | 7/1984 | McSpadden | |
| 4,538,989 A * | 9/1985 | Apairo et al. | 433/102 |
| 4,934,934 A * | 6/1990 | Arpaio et al. | 433/102 |
| 4,992,048 A | 2/1991 | Goof | |
| 5,503,554 A | 4/1996 | Schoeffel | |
| 5,605,460 A | 2/1997 | Heath et al. | |
| 5,676,541 A | 10/1997 | Maillefer et al. | |
| 5,842,862 A * | 12/1998 | Nissan | 433/102 |
| 5,882,198 A | 3/1999 | Taylor et al. | |
| 5,902,106 A | 5/1999 | McSpadden | |
| 5,921,775 A * | 7/1999 | Buchanan | 433/102 |
| 5,938,440 A | 8/1999 | McSpadden | |
| 6,106,296 A * | 8/2000 | Johnson | 433/224 |
| 6,299,445 B1 * | 10/2001 | Garman | 433/102 |
| 2004/0131993 A1 | 7/2004 | Rouiller et al. | 433/102 |

FOREIGN PATENT DOCUMENTS

| | | | | |
|---|---|---|---|---|
| EP | 0120542 | * | 10/1984 | 433/165 |
| WO | WO02/0659398 A1 | | 8/2002 | |

* cited by examiner

*Primary Examiner*—Cary E. O'Connor
(74) *Attorney, Agent, or Firm*—Fish & Richarson P.C.

(57) ABSTRACT

Methods and apparatus providing an endodontic instrument having a reversed helix. An endodontic instrument in accordance with the invention includes a shaft that includes an end, a tip, one or more flutes, and a longitudinal axis. At least one flute includes a cutting edge configured to cut when the shaft is rotated in a first direction of rotation about the longitudinal axis. The at least one flute spirals around the shaft in an end-to-tip longitudinal direction and in a second direction of rotation that is opposite from the first direction of rotation.

20 Claims, 15 Drawing Sheets

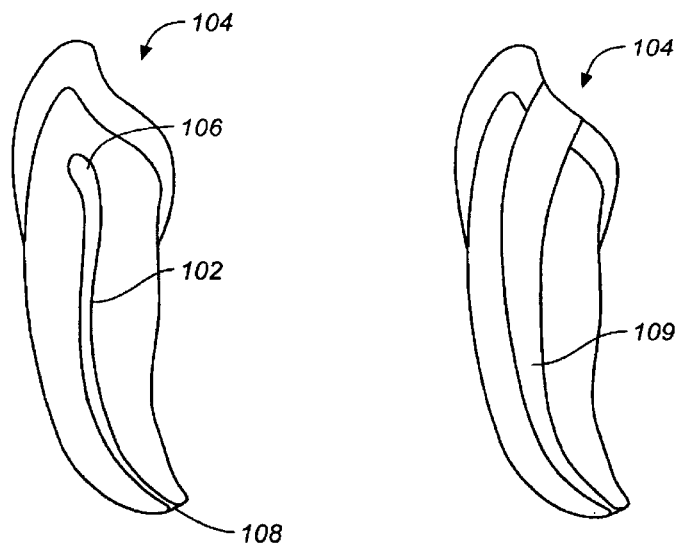
FIG._1A
*(PRIOR ART)*
FIG._1B
*(PRIOR ART)*
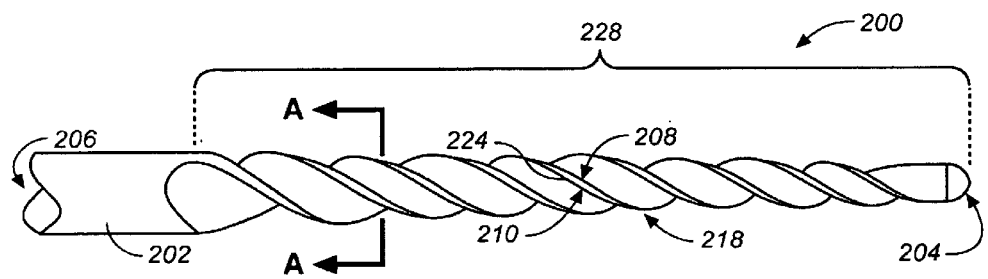
FIG._2A *(PRIOR ART)*
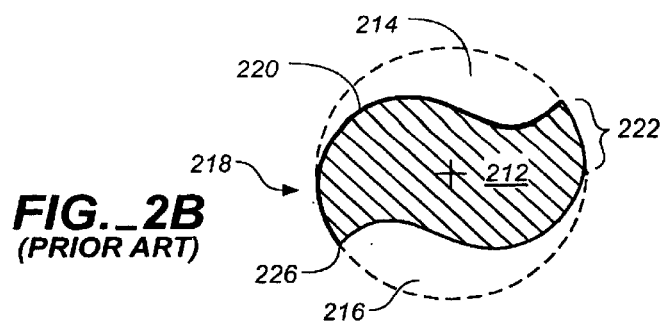
FIG._2B
*(PRIOR ART)*

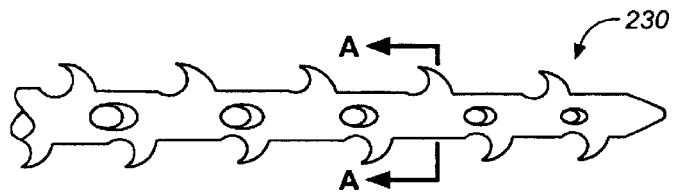
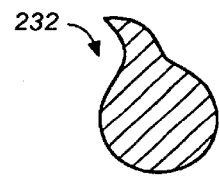
FIG._2C
*(PRIOR ART)*
FIG._2D
*(PRIOR ART)*
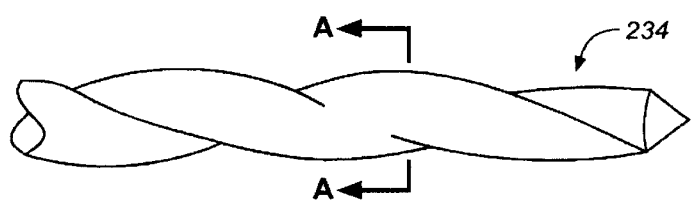
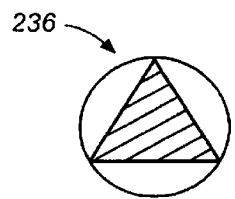
FIG._2E
*(PRIOR ART)*
FIG._2F
*(PRIOR ART)*
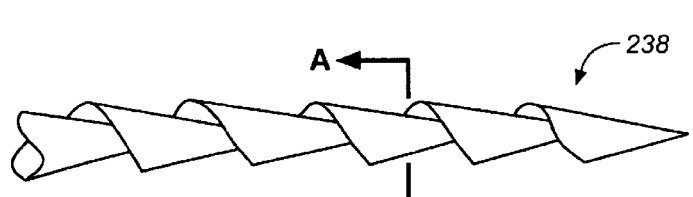
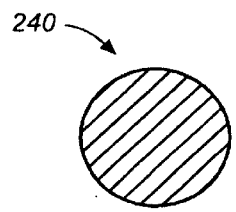
FIG._2G
*(PRIOR ART)*
FIG._2H
*(PRIOR ART)*
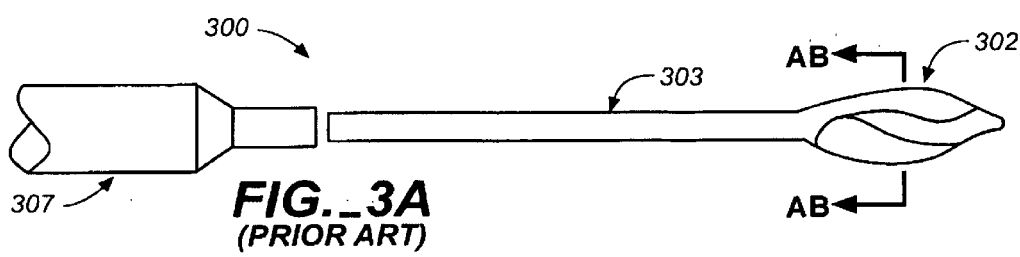
FIG._3A
*(PRIOR ART)*
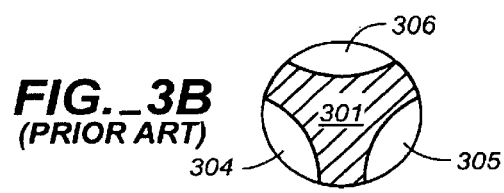
FIG._3B
*(PRIOR ART)*

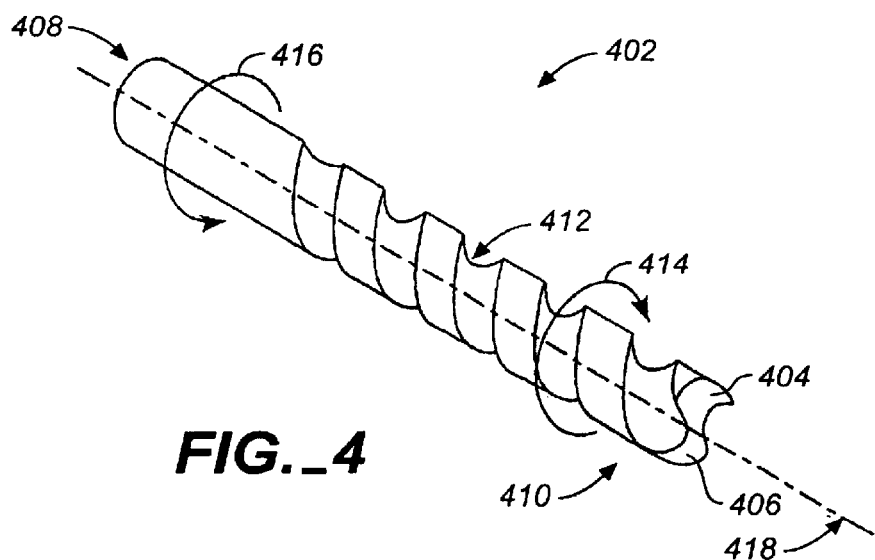
FIG._4
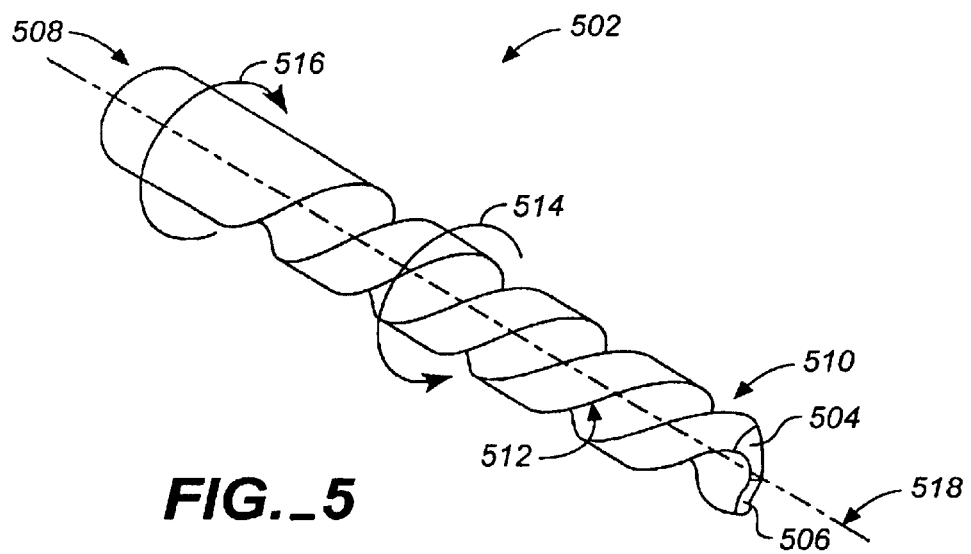
FIG._5

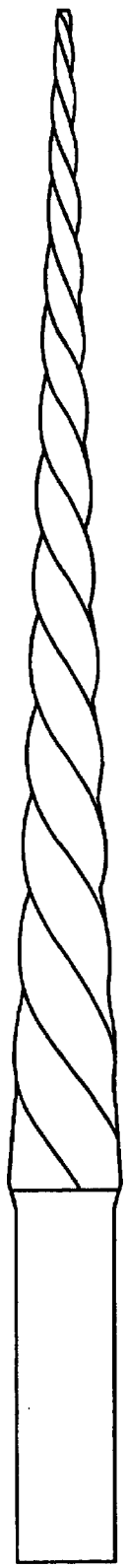
FIG._6A  FIG._6B

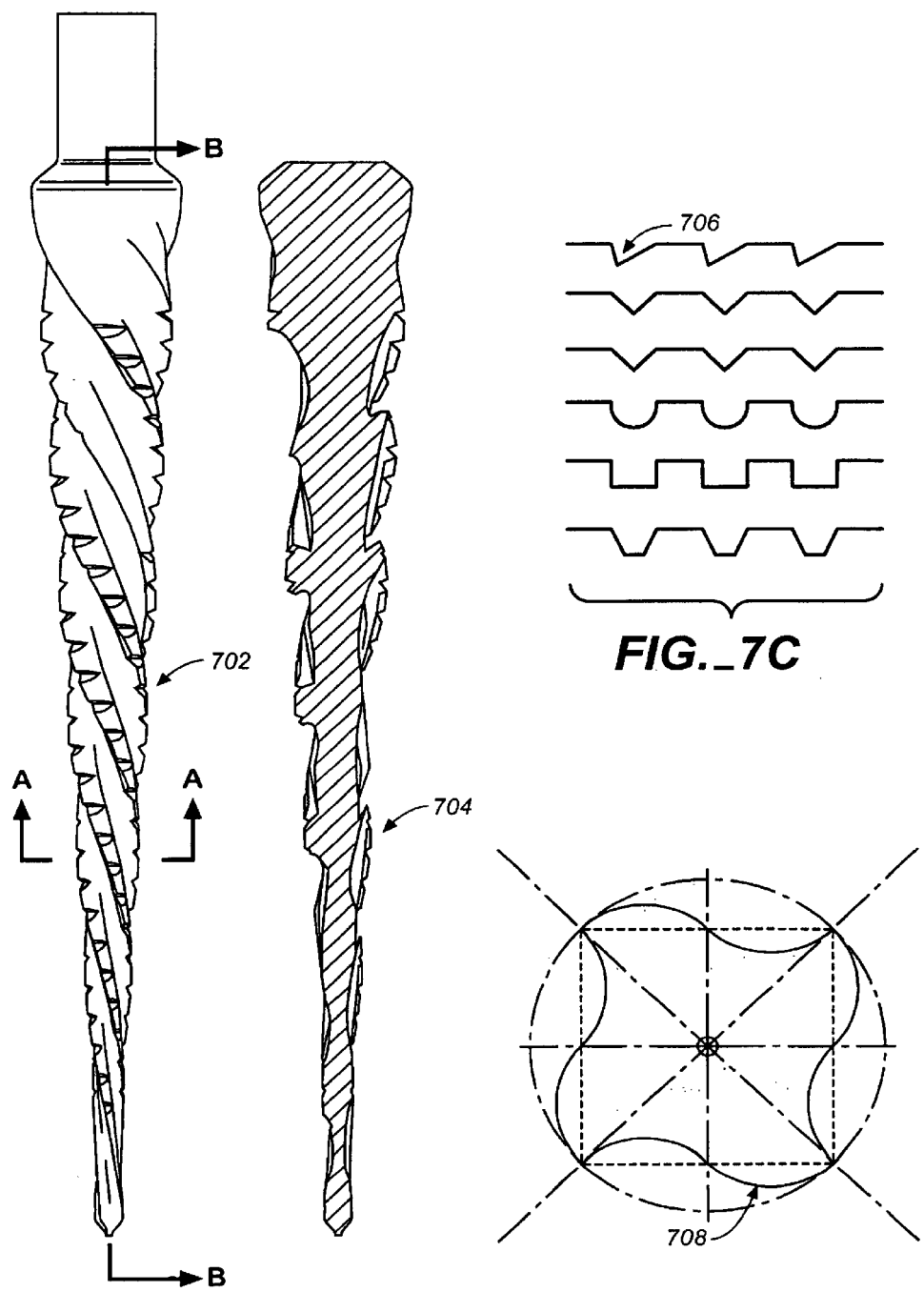
*FIG._7A*  *FIG._7B*  *FIG._7D*

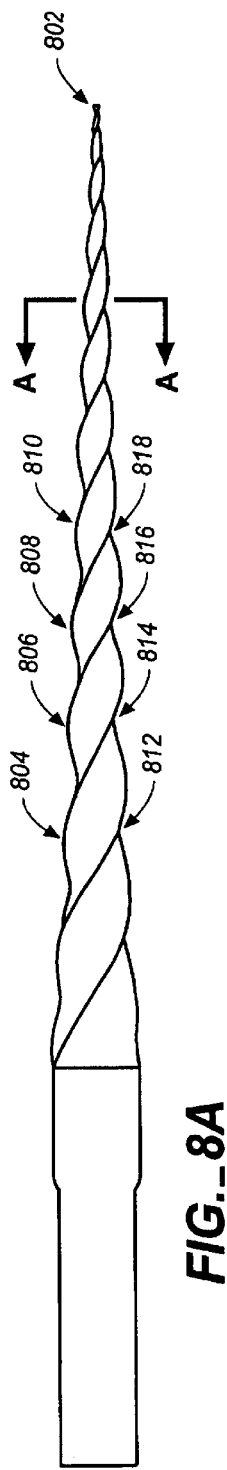
FIG._8A
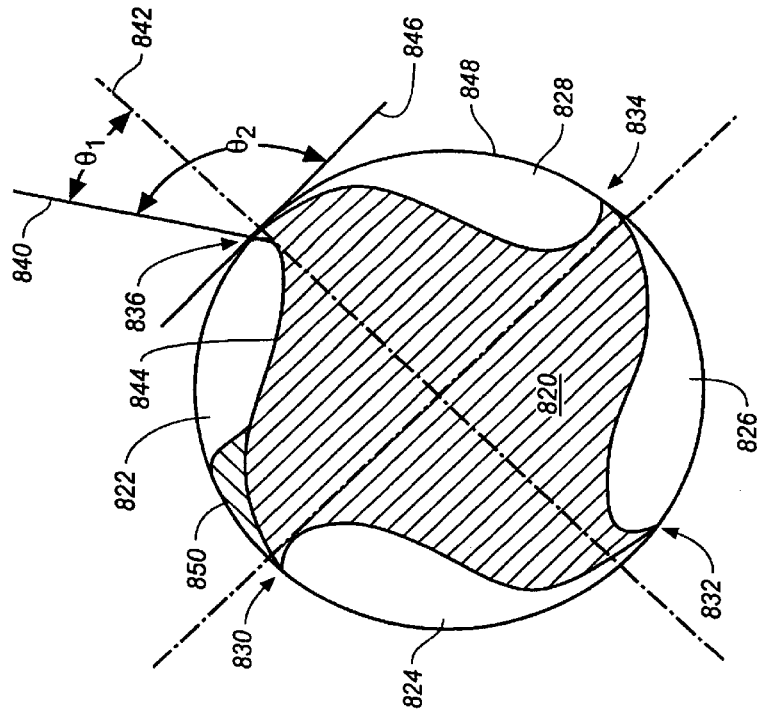
FIG._8B

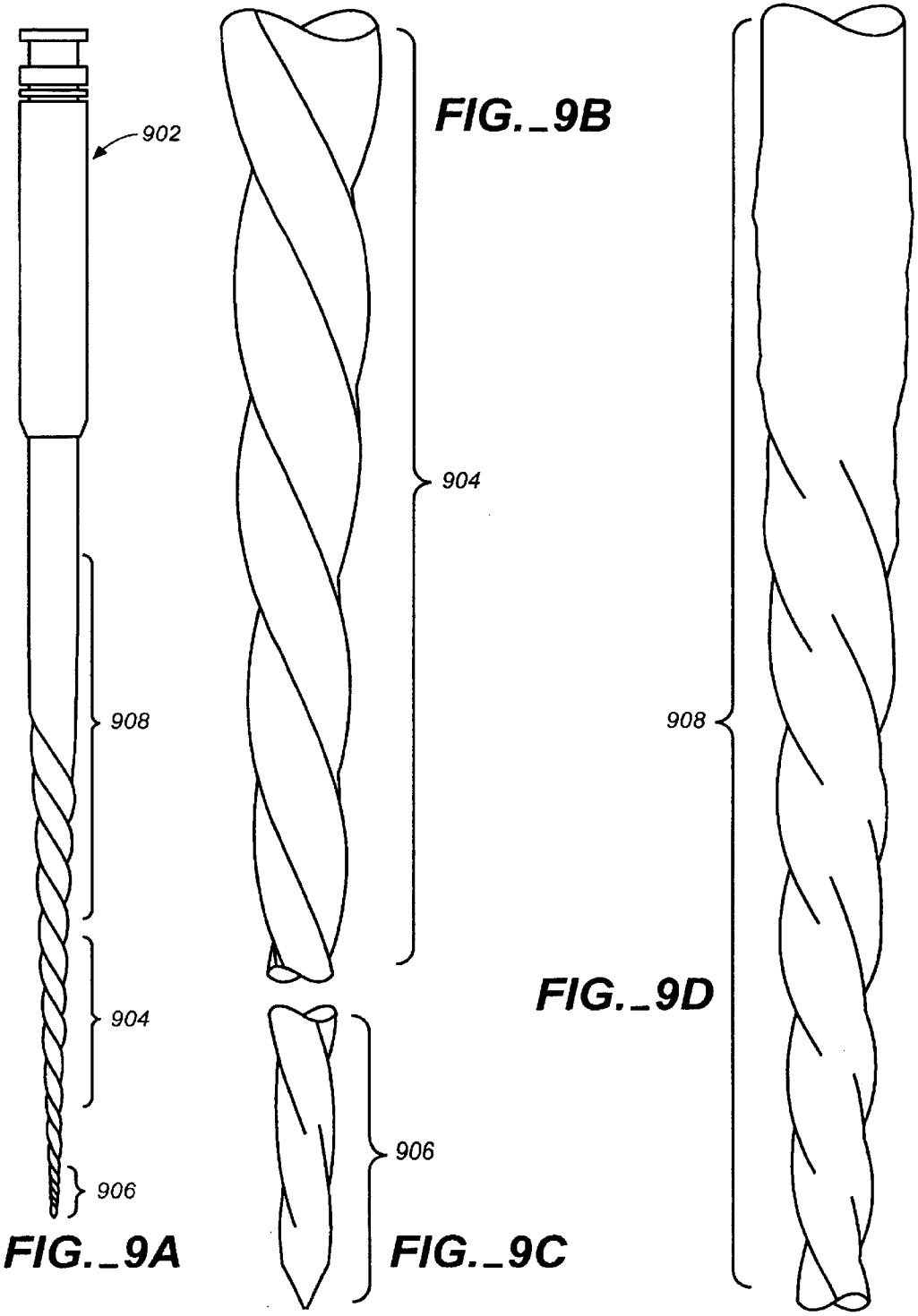

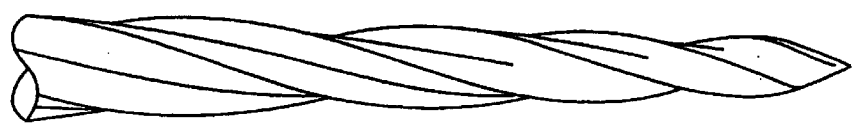
FIG._9E
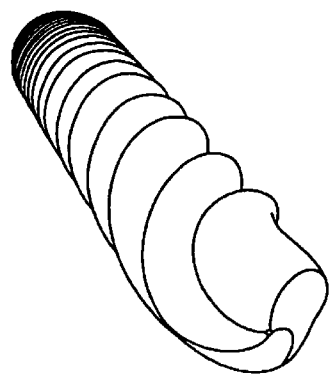
FIG._9F
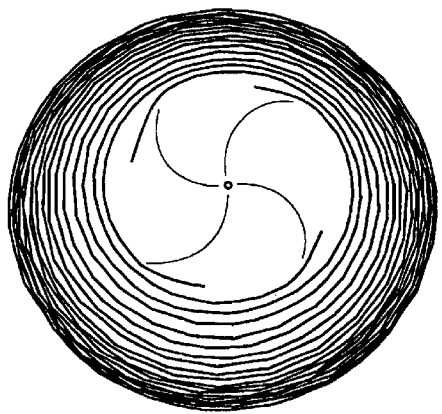
FIG._9G
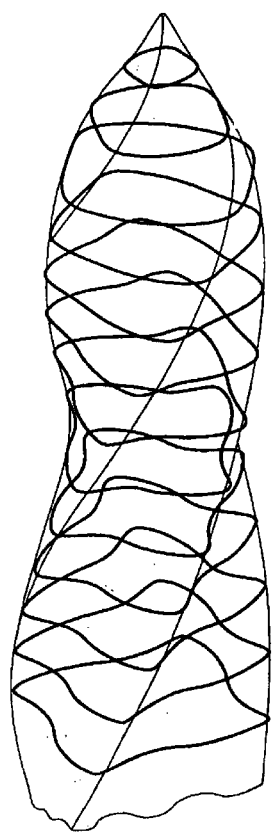
FIG._9H

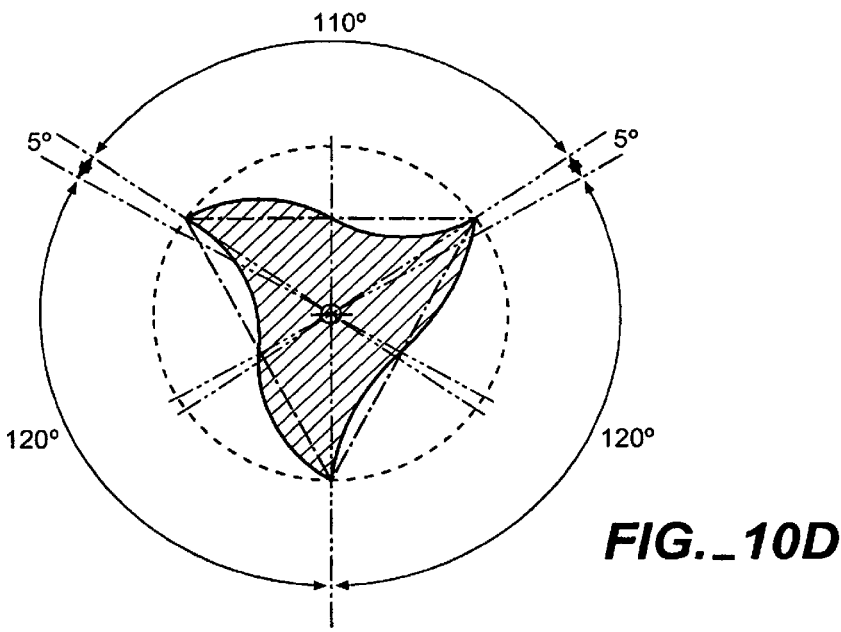
FIG._10D
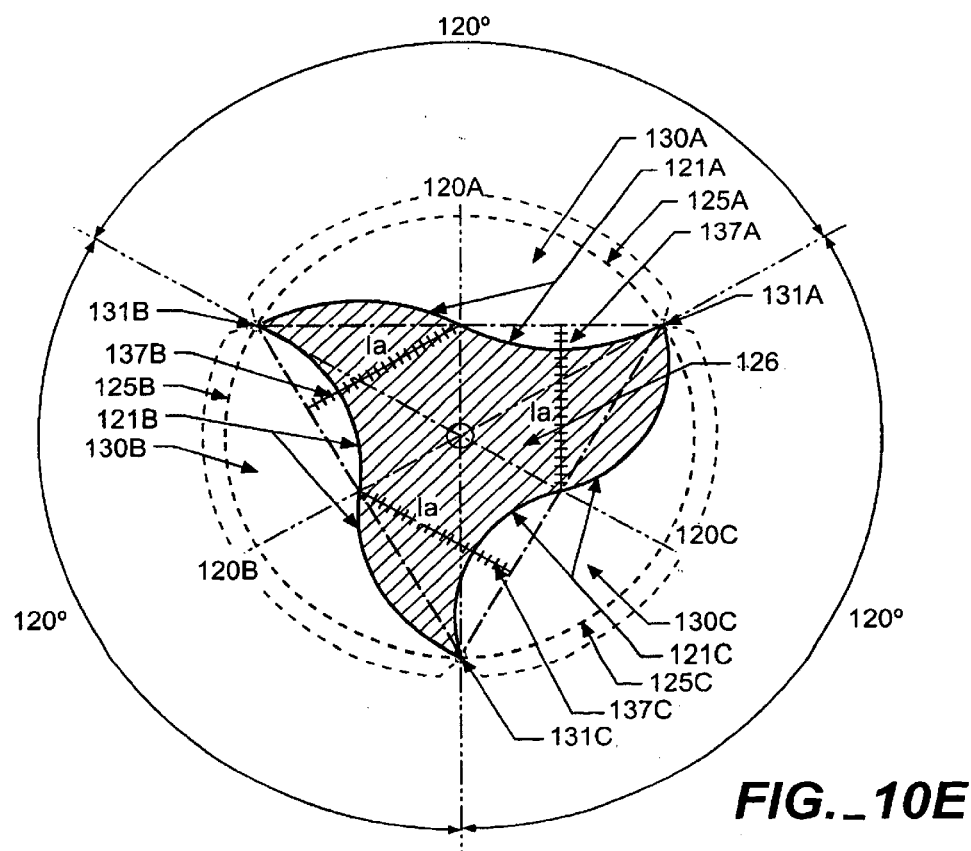
FIG._10E

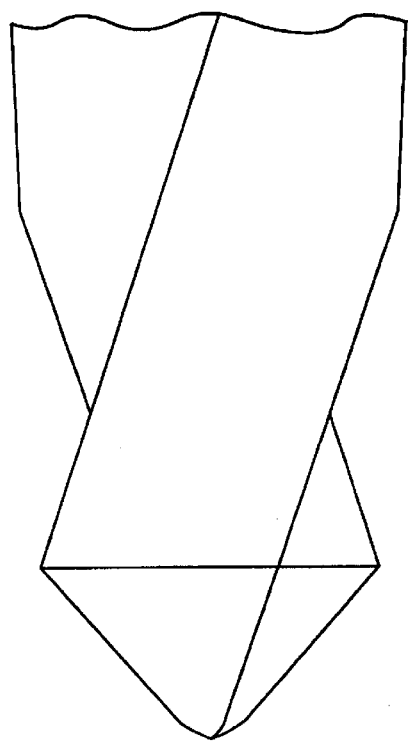
FIG._11A
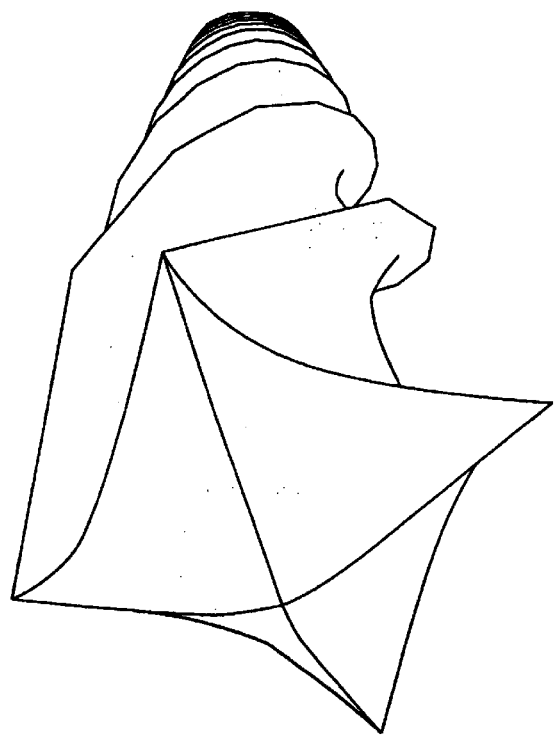
FIG._11D
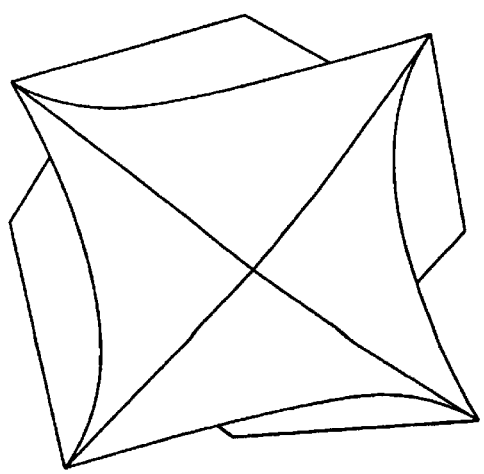
FIG._11B
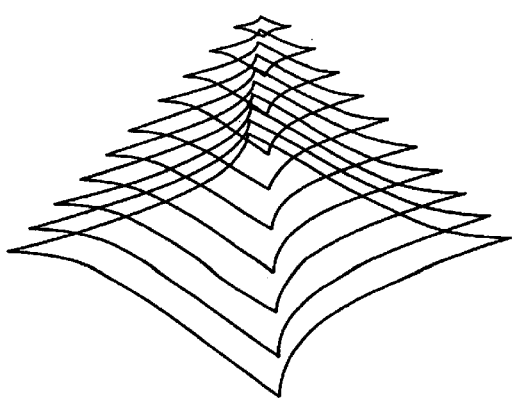
FIG._11C

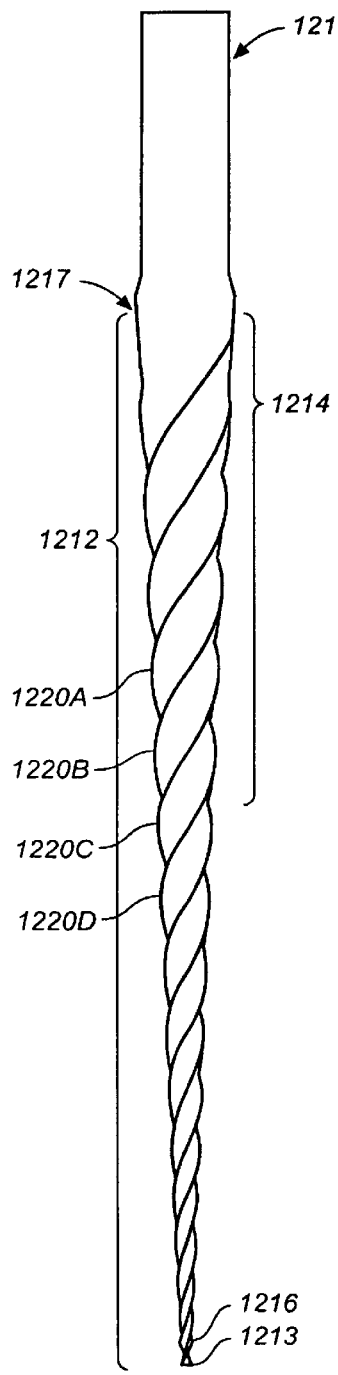
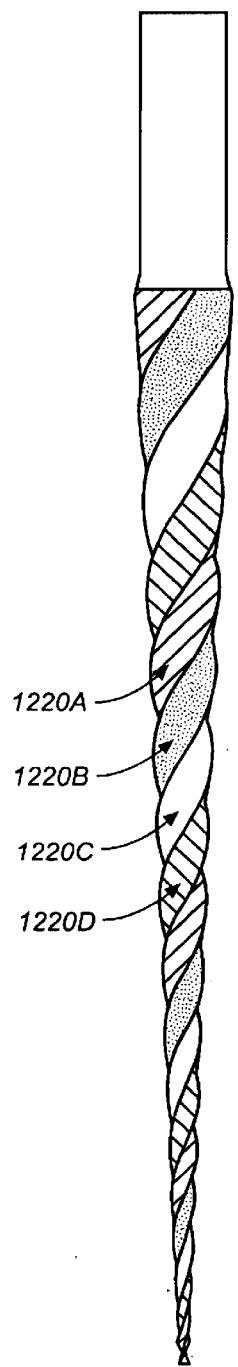
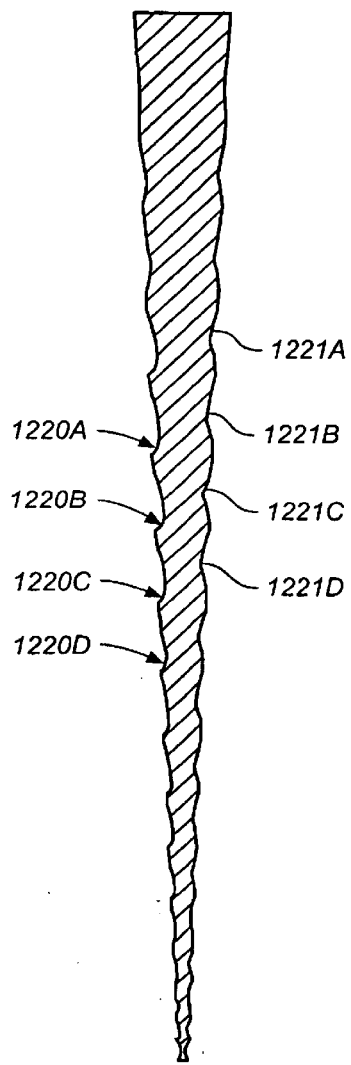
*FIG._12A*  *FIG._12B*  *FIG._12C*

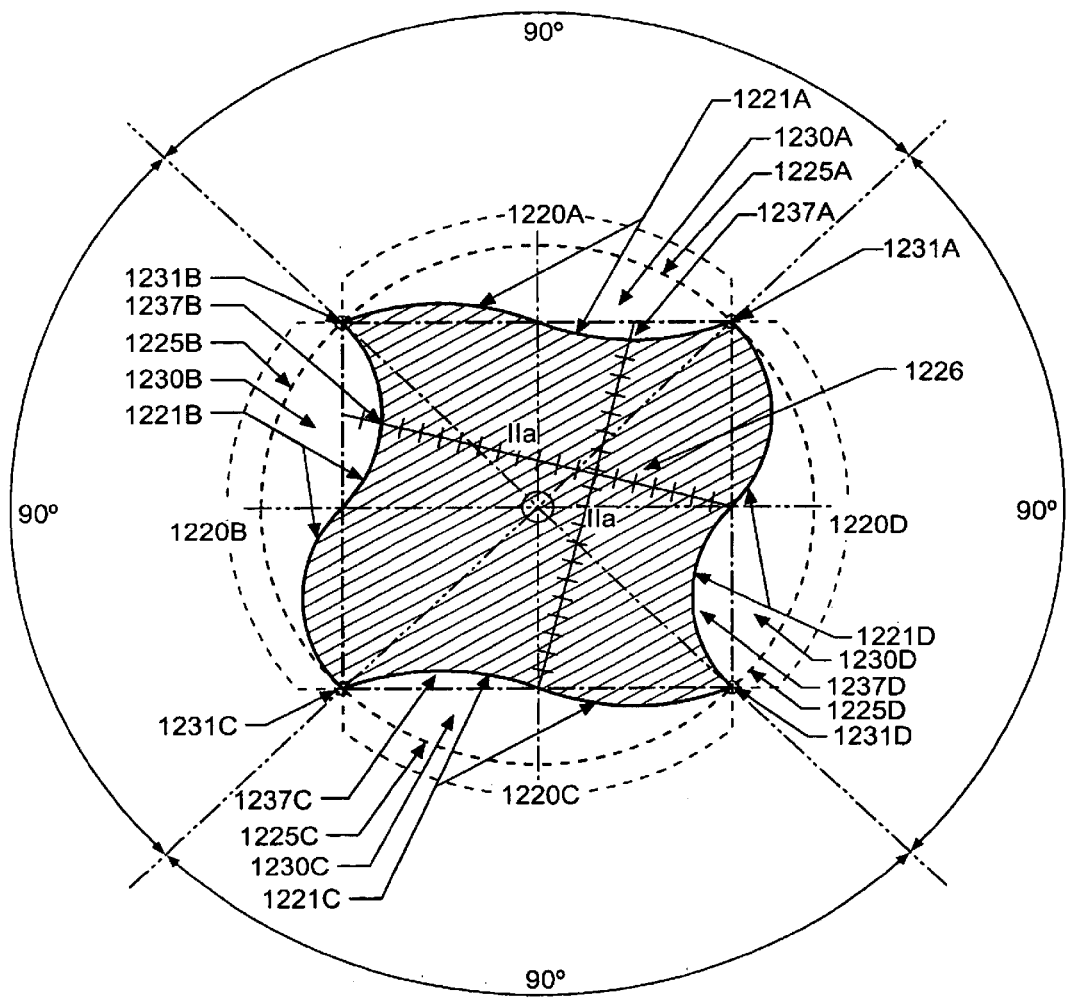
FIG._12D

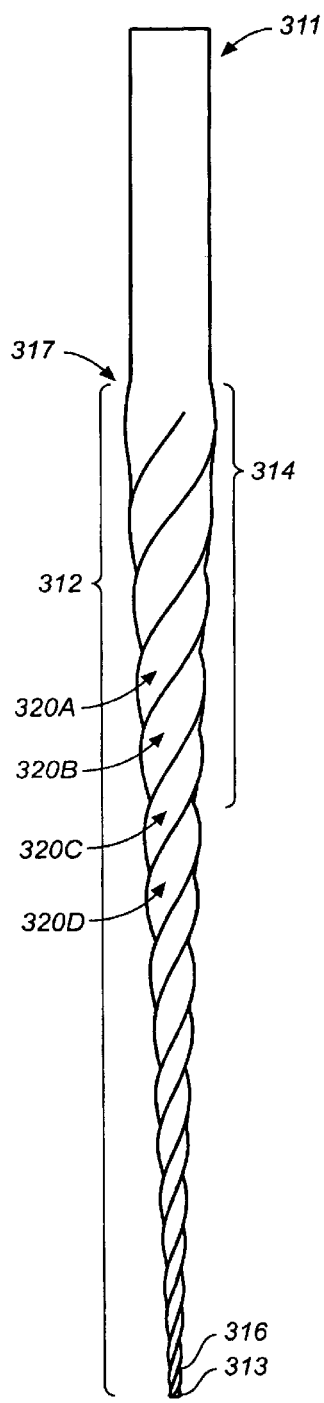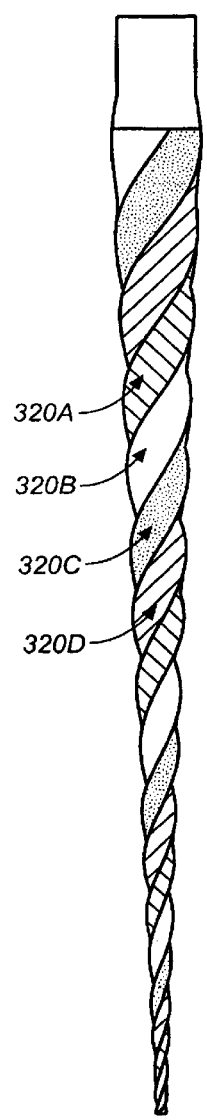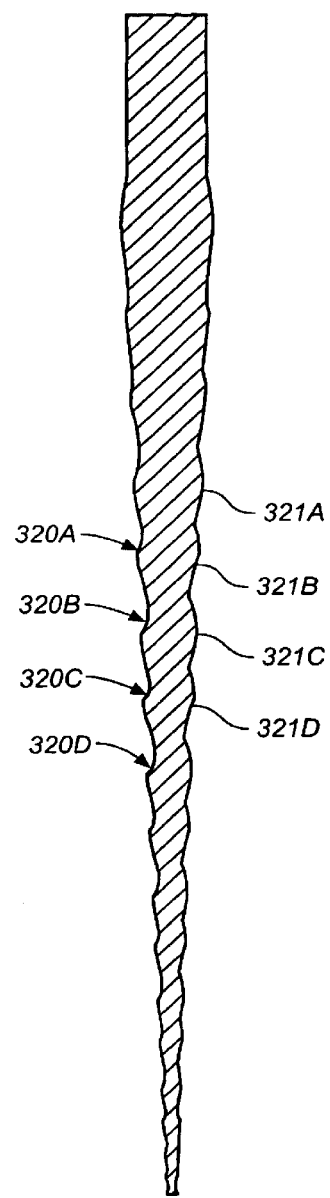
FIG._13A  FIG._13B  FIG._13C

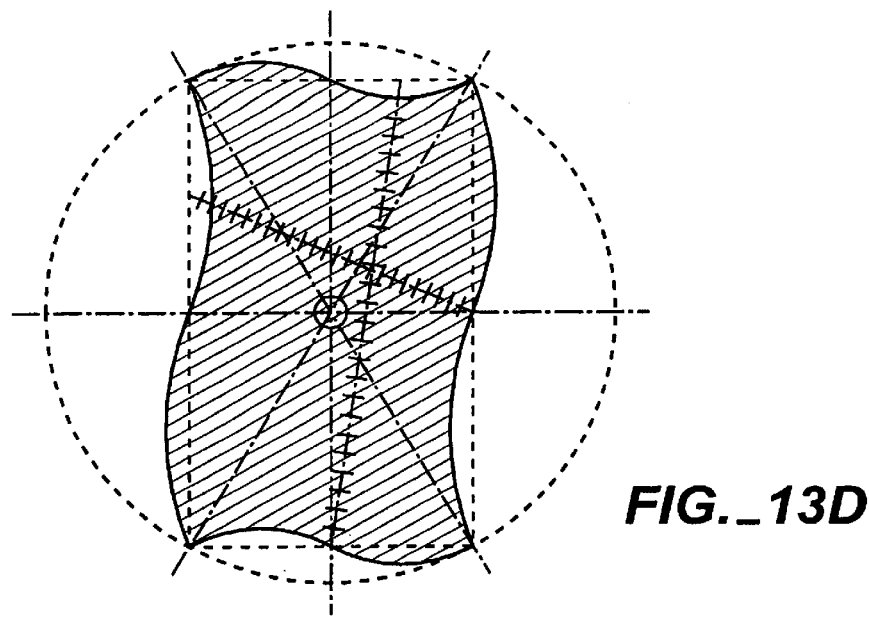
FIG._13D
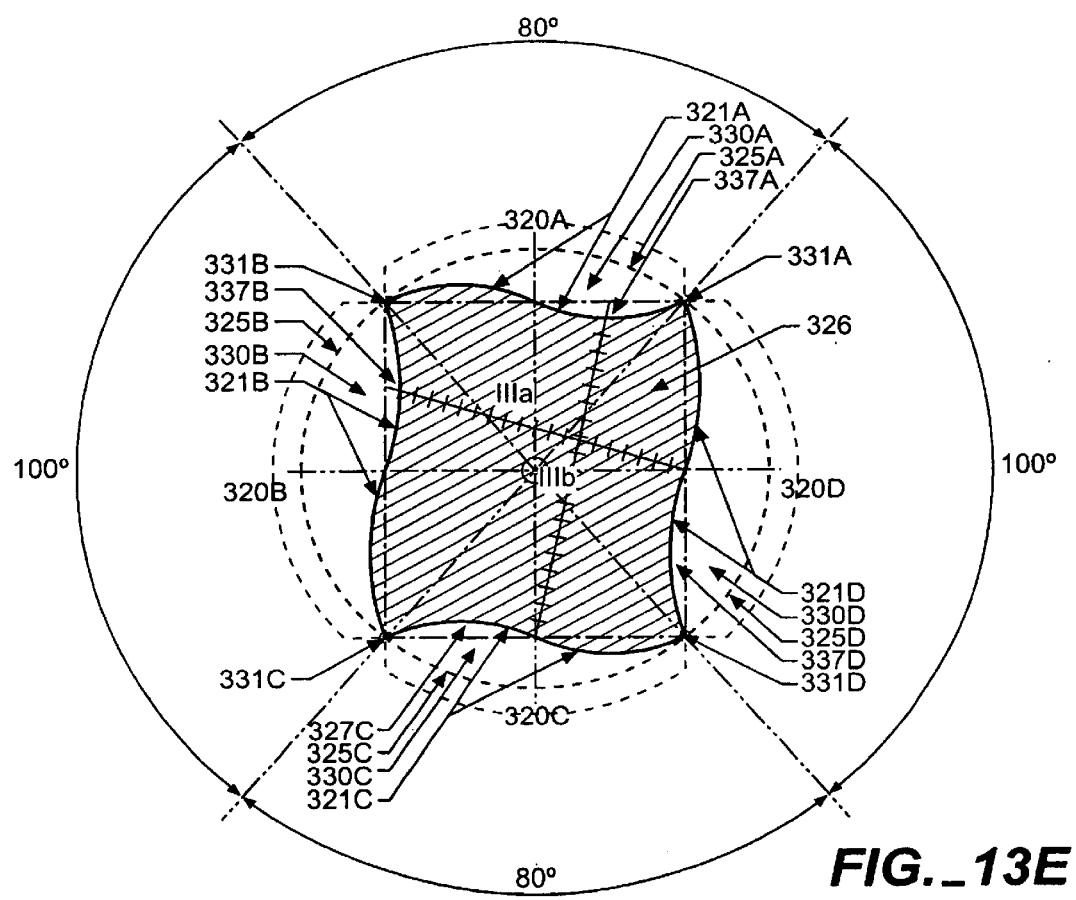
FIG._13E

ENDODONTIC INSTRUMENT HAVING REVERSED HELIX

This application claims the benefit of U.S. Provisional Applications Ser. No. 60/467,472, filed May 1, 2003, and Ser. No. 60/477,688, filed Jun. 10, 2003, which are hereby incorporated by reference in its entirety.

BACKGROUND

The present invention relates to endodontic instruments.

Endodontic instruments can be used for cleaning and enlarging the endodontic cavity space ("ECS"), also known as the root canal system of a human tooth. FIG. 1A shows an example of an unprepared root canal 102 of a tooth 104. As can be seen, the unprepared root canal 102 is usually a narrow channel that runs through the central portion of the root of the tooth. Cleaning and enlargement of the ECS can be necessitated by the death or necrosis of the dental pulp, which is the tissue that occupies that space in a healthy tooth. This tissue can degenerate for a multitude of reasons, which include tooth decay, deep dental restorations, complete and incomplete dental fractures, traumatic injuries or spontaneous necrosis due to the calcification and ischemia of the tissue, which usually accompanies the ageing process. Similar to a necrotic or gangrenous appendix, the complete removal of this tissue is paramount, if not urgent, because of the subsequent development of infections or dental abscesses, septicemia, and even death.

The root canal system of a human tooth is often narrow, curved and calcified, and can be extremely difficult to negotiate or clean. Indeed, the conventional endodontic or root canal instruments currently available are frequently inadequate in the complete removal of the pulp and the efficient enlargement of the ECS. Furthermore, they are usually predisposed to breakage, causing further destruction to the tooth. Broken instruments are usually difficult, if not impossible to remove, often necessitating the removal of the tooth. Injury to the tooth, which occurs as the result of a frank perforation or alteration of the natural anatomy of the ECS, can also lead to failure of the root canal and tooth loss.

A root canal procedure itself can be better appreciated by referring to FIGS. 1A and 1B. The unprepared root canal 102 of the tooth 104 usually begins as a narrow and relatively parallel channel. The portal of entry or the orifice 106 and the portal of exit or foramen 108 are relatively equal in diameter. To accommodate complete cleaning and filling of the canal and to prevent further infection, the canal must usually be prepared. The endodontic cavity preparation ("ECP") generally includes progressively enlarging the orifice and the body of the canal, while leaving the foramen relatively small. The result is usually a continuous conical shaped preparation, for example, the space 109.

In general, endodontic instruments are used to prepare the endodontic cavity space as described above. Endodontic instruments can include hand instruments and engine driven instruments. The latter can but need not be a rotary instrument. Combinations of both conventional hand and engine-driven rotary instruments are usually required to perform an ECP successfully and safely.

FIGS. 2A and 2B show a conventional endodontic instrument 200. The endodontic instrument shown includes a shaft 202 that includes a tip 204 and a shank 206. The endodontic instrument 200 also includes grooves 208 and 210 that spiral around the shaft 202. The grooves are referred to in the instant specification as flutes.

FIG. 2B shows a cross section 212 (i.e., cross section A—A) of the endodontic instrument. The cross section 208 shows cross sections 214 and 216 of flutes 208 and 210, respectively. As can be seen from FIGS. 2A and 2B, the flutes 208 and 210 are generally the spacing on both sides of a helical structure 218 (or helix) that spirals around the shaft 202. The bottom portion of a flute—seen as a line or curve (e.g., curve 220 indicated in bold)—is referred to in the instant specification as a spline (indicated by line in bold). The portion of a spline that comes into contact with a surface being cut during cutting will be referred to in the instant specification as a radial land. Item 222 of FIG. 2B is an example of a radial land.

A flute of an endodontic instrument usually includes a sharpened edge configured for cutting. Edge 224 of FIG. 2A is an example of such a cutting edge. Edge 224 can be seen as a point 226 in FIG. 2B. Generally, an instrument having right-handed cutting edges is one that will cut or remove material when rotated clockwise, as viewed from shank to tip. In this specification, a direction of rotation will be specified as viewed from the shank to the tip of the instrument. The cut direction of rotation for a right handed endodontic instrument is clockwise. An instrument having left-handed cutting edges is one that will cut or remove material when rotated counter-clockwise. The cut direction of rotation, in this case, is counter-clockwise.

An endodontic instrument includes a working portion, which is the portion that can cut or remove material. The working portion is typically the portion along the shaft that is between the tip of the instrument and the shank end of the flutes. Portion 228 is the working portion for the endodontic instrument shown in FIG. 2A. The working portion is also referred to in this specification as the cutting portion, and the working length as the cutting or working length.

Hand instruments are typically manufactured from metal wire blanks of varying sizes. The metallurgical properties of these wires, in general, have been engineered to produce a wide range of physical properties. These wires are usually then twisted or cut to produce specific shapes and styles. Examples of hand instruments include K-type, H-type, and R-type hand instruments. FIG. 2C show a barbed broach 230, which is one example of an R-type instrument. FIG. 2D shows a cross section 232 (i.e., cross section A—A) of the barbed broach 230. The barbed broach is manufactured from soft iron wire that is tapered and notched to form barbs or rasps along its surface. These instruments are generally used in the gross removal of pulp tissue or debris from the root canal system. Another R-type file is a rat-tail file.

K-type instruments in current usage include reamers and K-files. FIG. 2E shows an example of a K-file 234. FIG. 2F shows a cross section 236 (i.e., cross section A—A) of the K-file 234. K files are generally available in carbon steel, stainless steel, and more recently, an alloy of nickel-titanium. To fabricate a K-type instrument, a round wire of varying diameters is usually grounded into three or four-sided pyramidal blanks and then rotated or twisted into the appropriate shapes. These shapes are specified and controlled by the American National Standards Institute ("ANSI") and the International Standards Organization ("ISO"). The manufacturing processes for reamers and files are similar; except however, files usually have a greater number of flutes per unit length than reamers. Reamers are used in a rotational direction only, whereas files can be used in a rotational or push-pull fashion. Files made from three-sided or triangular blanks have smaller cross sectional areas than files made from four-sided blanks. Thus, these instruments are usually more flexible and less likely to fracture. They also can display larger clearance angles and are more efficient during debridement. Triangular files, therefore, are generally considered more desirable for hand instrumentation.

FIG. 2G shows an example of an H-type file 238. FIG. 2H shows a cross section 240 (i.e., cross section A—A) of the H-type file 238. H-type files are usually manufactured by grinding flutes into tapered round metal blanks to form a series of intersecting cones. H-type files can usually cut only in the pull direction (i.e., a pull stroke). Primarily because they have positive cutting angles, H-type files can be extremely efficient cutting instruments.

Hand instruments are usually manufactured according to guidelines of the ANSI and the ISO, which specified that a working portion of an instrument be 16 mm in length. ANSI and ISO further specified that a first diameter or $D_1$ of the instrument, be 1 mm from the tip or $D_0$. Other ANSI and ISO specifications require that: instruments have a standard taper of 0.02 mm per mm along the working portion 216; the tip maintain a pyramidal shape no greater than 75° in linear cross section; and hand instruments (e.g., the ones shown in FIGS. 2A–2H) be available in 21, 25, and 31 mm lengths.

In addition to the hand instruments described above, there are rotary instruments that are usually motor driven. FIG. 3A shows an example rotary instrument 300 that is referred to as a G-type reamer or drill. FIG. 3B shows a cross section 301 (i.e., cross section A—A) of the G-type instrument. G-type drills are usually available in carbon or stainless steel. As is typical, the G-type drill 300 shown includes a short flame-shaped head 302 attached to a long shank 303. The core or web shown in FIG. 3B shows the cross sections 304, 305, and 306 of three flutes. The flutes, in this instance, have U-shaped splines. The instrument 300 includes cutting edges that have negative rake-angles. In general, a rake angle is the angle between the leading edge of a cutting tool and a perpendicular to the surface being cut. Rake angle is further described below. The flame-shaped head 302 includes a non-cutting surface to prevent perforation. The instrument 300 is usually used as a side-cutting instrument only. The instrument 300 is relatively rigid and, therefore, cannot usually be used in a curved space, for example, the ECS.

G-type drills are available in 14, 18 and 25 mm lengths as measured from tip to shank, which is where the drill can be inserted into a standard slow-speed hand piece via a latch grip 307. G-type drills are available in varying diameters of 0.30 mm to 1.5 mm and from sizes 1 through 6.

SUMMARY

The present invention provides methods and apparatus for providing an endodontic instrument having a reversed helix.

In general, in one aspect, the invention provides an endodontic instrument that includes a shaft that includes an end, a tip, one or more flutes, and a longitudinal axis. At least one flute includes a cutting edge configured to cut when the shaft is rotated in a first direction of rotation about the longitudinal axis. The at least one flute spirals around the shaft in an end-to-tip longitudinal direction and in a second direction of rotation that is opposite from the first direction of rotation.

In general, in another aspect, the invention provides an endodontic instrument that includes a shaft that includes an end, a tip, one or more flutes, and a longitudinal axis, wherein at least one flute includes a cutting edge configured to cut when the shaft is rotated in a first direction of rotation about the longitudinal axis, wherein the at least one flute is situated to wrap around the shaft in an end-to-tip longitudinal direction and in a second direction of rotation that is opposite from the first direction of rotation, wherein the at least one flute includes one or more cross cuts, and wherein the at least one flute has one of reduced or no radial lands.

In general, in another aspect, the invention provides an endodontic instrument that includes a shaft that includes an end, a tip, one or more flutes, and a longitudinal axis, wherein at least one flute includes a cutting edge configured to cut when the shaft is rotated in a first direction of rotation about the longitudinal axis, and wherein the at least one flute is situated to wrap around the shaft in an end-to-tip longitudinal direction and in a second direction of rotation that is opposite from the first direction of rotation.

The invention can be implemented to realize one or more of the following advantages. An endodontic instrument configured as described in this specification has improved flexibility to allow the instrument to negotiate the tortuous, complex bends of a root canal. The instrument has improved cutting ability to allow the instrument to clean and enlarge the root canal efficiently. The endodontic instrument described, for example, includes features that allow the use of higher cutting torque and cutting speeds. The instrument has improved carriage capacity to haul debris to the coronal aspect of the tooth efficiently. The instrument has improved restoring force or resistance to bending to maintain the integrity of the instrument. The instrument has significant improved resistance to premature fatigue or breakage. The instrument has improved escapement and resistance to binding in the canal.

The details of one or more implementations of the invention are set forth in the accompanying drawings and the description below. Other features and advantages of the invention will become apparent from the description and the drawings.

BRIEF DESCRIPTION OF THE DRAWINGS

FIGS. 1A and 1B illustrate a root canal procedure.

FIGS. 2A–2H show examples of endodontic instruments.

FIGS. 3A and 3B show an example of a rotary-type endodontic instrument.

FIG. 4 shows an endodontic instrument having reversed helices.

FIG. 5 shows another endodontic instrument having reversed helices.

FIGS. 6A and 6B show other endodontic instruments having a reversed helices.

FIGS. 7A–7D show an endodontic instrument having cross cuts on its helices.

FIGS. 8A and 8B show an endodontic instrument having S-splines, positive cutting angles, and none or reduced radial lands.

FIGS. 9A–9H show an endodontic instrument having rolled edges and tapering.

FIGS. 10A–10E show one implementation of an endodontic instrument.

FIGS. 11A–11D show an endodontic instrument that includes a cutting tip.

FIGS. 12A–12D show another implementation of an endodontic instrument.

FIGS. 13A–13E show another implementation of an endodontic instrument.

Like reference numbers and designations in the various drawings indicate like elements.

DETAILED DESCRIPTION

Reversed Helix

Figures 10A, 10B, 10C:
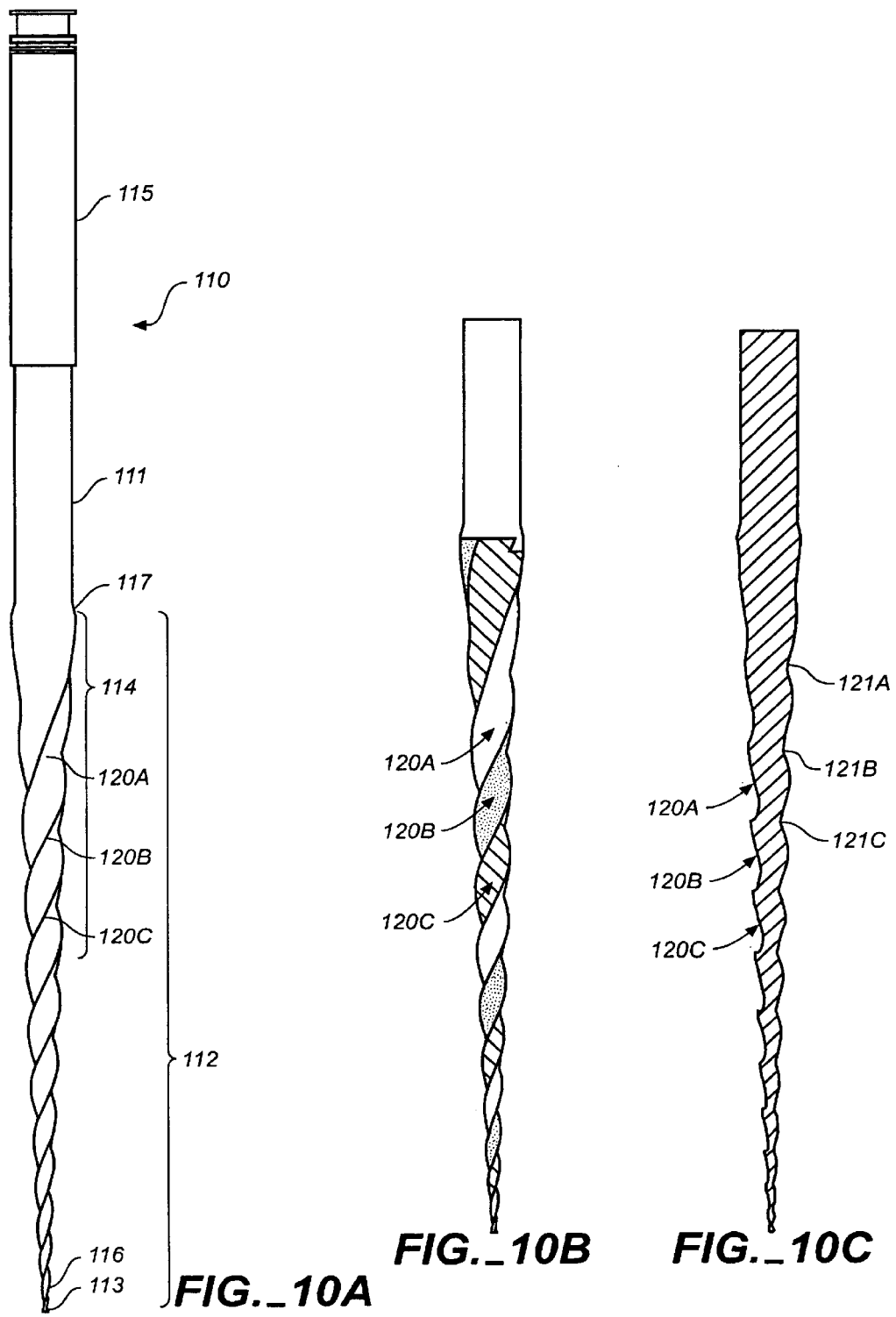

Conventional endodontic instruments have right-handed cutting edges and right-handed helices. A flute that forms a right handed helix spirals around the shaft, in a shank-to-tip longitudinal direction and, furthermore, in a clockwise direction of rotation (as viewed from shank to tip). This configuration is similar to the treads of a screw. Conventional endodontic instruments having this screw-like configuration are prone to binding. Furthermore, the radial lands and negative cutting angles typical of convention endodontic instruments predisposed the instruments to premature fatigue and breakage.

An endodontic instrument in accordance with the invention can include a reversed helix. A reversed helix spirals around the shaft of an instrument, in an shank-to-tip longitudinal direction and, furthermore, in a direction of rotation opposite to the cut direction of rotation. If, for example, the endodontic instrument has a clockwise cut direction of rotation, its helices would spiral in a counter-clockwise direction of rotation (along a longitudinal axis of the shaft in a shank-to-tip direction and as viewed from shank to tip). In this case, the instrument includes right-handed cutting edges. That is, the cutting edge is on the leading edge side of the helices as the instrument is rotated in the cut direction of rotation.

FIG. 4 shows an example of the described endodontic instrument. The instrument shown includes a shaft 402, helices 404 and 406, shank end (or simply end) 408, tip end (or simply tip) 410. The helix 406, for example, includes cutting edge 412. Thus, the instrument cuts when it is rotated about its longitudinal axis 418 in a counter-clockwise direction (as seen from an end-to-tip perspective), and the cut direction is counter-clockwise (as indicated by arrow 414). The direction which helices 404 and 406 spiral around the shaft 402 is clockwise (along the shaft in an end-to-tip direction and as viewed from an end-to-tip perspective; as indicated by arrow 416).

If the endodontic instrument has a clockwise cut direction of rotation (as seen from an end-to-tip perspective), then its flutes can spiral in a counter-clockwise direction of rotation (along a longitudinal axis of the shaft in an end-to-tip direction; and as viewed from an end-to-tip perspective). FIG. 5 shows and example of the described endodontic instrument. The instrument shown includes a shaft 502, helices 504 and 506, shank end (or simply end) 508, tip end (or simply tip) 510. The helix 504, for example, includes cutting edge 512. Thus, the instrument cuts when it is rotated about its longitudinal axis 518 in a clockwise direction (as seen from an end-to-tip perspective), and the cut direction is clockwise (as indicated by arrow 514). The direction which flutes 504 and 506 spiral around the shaft 502 is counter-clockwise (along the shaft in an end-to-tip direction and as viewed from an end-to-tip perspective; as indicated by arrow 516).

An endodontic instrument having the reversed helix is generally not prone to binding and can haul debris from its tip to its end, thus removing the debris from the space being prepared. In one implementation, the endodontic instrument can be fabricated from Ni—Ti or a Ni—Ti alloy. Engine driven instruments, including rotary engine driven instruments, as well as hand instruments can include the described reversed helix configuration.

In the above examples, the endodontic instruments shown included only two flutes. Endodontic instruments having any number of flutes and any spline geometry can incorporate the described reversed helix configuration. FIGS. 6A and 6B show implementations of multiple flute endodontic instruments having the reversed helix configuration.

Helices Having Cross Cuts

An endodontic instrument in accordance with the invention can include helices that include one or more cross cuts. The cross cuts of a helix can but need not be at right angles to the helix. In general, the cross cuts can have a geometry and depth so as to increase the flexibility of the endodontic instrument and allow the instrument to bend more easily. FIG. 7A shows an instrument 702 that includes helices having cross cuts. FIG. 7B shows a cross section 704 (i.e., cross section B—B) of the instrument 702. FIG. 7C shows the different example geometries which a cross cut can have. The cross cuts can include cutting edges, for example, cutting edge 706, which consequently provide a more efficient cutting device. FIG. 7D shows a cross section 708 (i.e., cross section A—A) of the instrument 702.

Web Designs Having S-Shaped Splines, Positive Cutting Angles, and None or Reduced Radial Lands FIG. 8A shows an instrument 802, which is one example an endodontic instrument having an S-shaped spline, positive cutting angles, and none or reduced radial lands. The instrument 802 includes four helices 804, 806, 808, and 810 and four flutes 812, 814, 816, and 818. FIG. 8B shows a cross section 820 (i.e., cross section A—A) of the instrument 802. The web design shown exhibits a quadrilateral-like shape. FIG. 8B shows cross sections 822, 824, 826, and 828 of the flutes. The splines are S-shaped, which provides mass that can buttress the cutting edges of the instrument.

The cutting edges (shown as four arcs delimited by points 830, 832, 834, and 836) can have reduced positive cutting angles, which makes the cutting edges less prone to breakage than cuttings edge with large cutting angles. In the instant specification, a cutting angle of a cutting edge that is formed by a flute can be defined as the angle between (i) a tangent of the spline of the flute at the cutting edge and (ii) a ray extending radially outward from the center of cross section of the instrument. For example, the cutting edge at point 836 that is formed by flute 822 exhibits a cutting angle $\theta_1$ defined by tangent 840 and ray 842. Tangent 840 can be mathematically represented as a one-sided derivative, taken at point 836, of a function that represents the spline 844. Alternatively, there are other ways of defining cutting angle. For example, the cutting angle can be defined as the angle $\theta_2$ between the described tangent 840 and a tangent 846 of a circumference 848 of the instrument at point 836. Under the alternative definition, the cutting angle $\theta_2$ is said to be neutral or zero when the angle is ninety degrees, positive when greater than ninety degrees, and negative when less than ninety degrees.

An S-shaped spline also removes the radial land usually present in conventional endodontic instruments. The crossed hatched area 850 represents a hypothetical radial land. As can be seen, the radial land, if present, would rub against a surface being cut and create unnecessary drag along the working surface of the instrument and render it inefficient and predisposed to breakage.

The described endodontic instrument can be fabricated from a preformed cylindrical metal blanks of nickel titanium. Alternatively, the instrument can be fabricated from others blanks and other materials.

The shank end of the above described instrument can include a latch-type attachment suitable for coupling, usually detachably, to a motor driven chuck. The latch-type attachment can also be suitable for coupling to a handle if the instrument is to be used manually. The tip of the instrument can be smooth while maintaining the conicity, taper, and transverse cross-sectional shape of the instrument.

The following describes an implementation. The tip of the implementation ends in a pyramidal or parabolic shape and is at least 0.05 mm in diameter and 1–3 mm in length. The cutting length (not including the tip) of the implementation is 8–16 mm in length. In general, the cutting length should be at least 2 mm in length. The cutting edges of the implementation is created by including one to six flutes. Alternatively, the implementation can include additional flutes. The flutes usually begin at a first position near the shank end of the instrument and ends at a second position near the tip end of the instrument. The first position is referred to as a maximum flute diameter (or MxFD) and the second position is referred to as a minimum flute diameter (or MnFD). The flutes are concave and are substantially the same as each other. The flutes have a shape and depth that remains constant along the length of the shaft. Alternatively, the shape and/or depth can vary along the length of the shaft. These flutes are spaced along the circumference of the cutting surface. The spacing can be of uniform intervals or irregular intervals. That is, the helix formation or spirals that progress from the shank end to the tip of the instrument can be spaced at regular intervals or increasingly narrower intervals. In the latter case, a greater number of spirals can be included per unit length along the longitudinal axis of the implementation. Each flute forms a neutral or slightly positive cutting angle. The flutes spiral around the shaft of the instrument, completing 360° of rotation for a minimum of 1 mm, and a maximum of 6 mm of axial length of the cutting surface.

Variable Working Surfaces With Flute Modifications and/or Attenuated Cutting Edges The working surfaces or leading edges of conventional endodontic instruments have been manufactured with active or sharp cutting edges along the entire length of the working surface. This configuration can predispose the instrument to great amounts of torque leading to premature fatigue and breakage. One can mitigate the problem by varying the taper and the length of the working surface. As the instrument increased in diameter, the length of the working surface, or the number of cutting flutes (i.e., the number of flutes that form cutting edges) per unit length along the longitudinal axis of the instrument, can be reduced. Although, this configuration does mitigate the amount of torque that the instrument engenders as the size of the instrument increases, eliminating flutes also eliminates the ability of the instrument to continue to haul debris coronally. As a result, the instrument can become easily clogged creating unnecessary drag on the instrument.

An endodontic instrument in accordance with the invention retains the flutes along the entire length of the working surface to maintain hauling action. The leading edge or the working surface, however, is modified such that only a portion of the working surface cuts. This modification is brought about by blunting or rolling the edge of flutes both at the tip and shank ends of the instrument, leaving the central portion of the cutting surface active. Rolling edges will prevent the instrument from over-enlarging or tearing the foramen of the ECS distally and mitigate drag and pre-mature fatigue proximally. FIGS. 9A–9D show an example instrument that includes a reduced working portion. FIG. 9A shows the instrument 902. FIG. 9B shows the working portion 904 of the instrument 902. FIG. 9C shows a non-cutting tip portion 906 of the instrument 902. FIG. 9D shows a non-cutting shank-end portion 908 of the instrument 902. FIGS. 9E–9H show an implementation in which the instrument 902 tapers from shank to tip.

Endodontic instruments can be provided in sets. A set usually includes instruments of different diameters. In preparing an ECS, an endodontist usually begins the preparation process using the instrument having the smallest diameter. As the ECS is enlarged, the endodontist usually switches to instruments of progressively larger diameters. The rolled edges feature described above can vary from one instrument to another in a set of instruments, with the active surface diminishing in length progressively as the diameter of the instrument increased. This feature would allow the instrument to continue to haul debris coronally, but mitigate the torque that the instrument is subject to when cutting.

Implementations

FIGS. 10A–10E illustrate one implementation. The endodontic instrument 110 includes three sides, is triangular in transverse cross-section, and can be utilized to remove tissue and/or dentin from an ECS. The instrument 110 includes a shank 111 and a working portion 112, which is tapered in a shank-to-tip direction. The tip 113 includes an active or cutting surface, which is confluent the working surface 112 (for example, like the tip shown in FIGS. 11A–11D). Alternatively, the leading tip 113 (of the instrument shown in FIGS. 10A–10E) can include a non-active or non-cutting surface, which is also confluent with the working surface 112 (for example, like the tip shown in FIG. 9C). The MxFD 117 is located near the shank end of the cutting surface and MnFD 116 is located near the tip 113. The shank 111 above the working portion 112 is essentially cylindrical and exhibits a slightly smaller diameter than the cutting surface at the MxFD. The instrument 110 includes rolled-edge portion 114, which is confluent with the working portion 112. This rolled-edge modification is illustrated in FIGS. 9A–9D. A fitting 115, which is suitable for an engine driven motor with a hand-piece and chuck, or a handle utilized for manual instrumentation, is attached to the shank 111.

As shown in FIGS. 10A–10E, three continuous helical flutes 120A, 120B and 120C are substantially concave grooves which follow the circumference of the working surface 112 spiraling toward the leading tip 113 forming concentric circles. These flutes may be equidistant from each other or become increasingly tighter or more numerous as they approach the tip. The total number of flutes from MxFD to the MnFD should be no fewer than 16 but not greater than 24. Helical flutes 120A, 120B and 120C each originate at the MxFD at separate locations that are equally spaced apart around the circumference of the shank 111 or more specifically at 120° of separation. Each helical structure (i.e., the mass between the flutes) is continuous along the length of the cutting surface 112 to the leading tip 113.

With reference to FIG. 10E, it can be seen that flutes 120A, 120B and 120C have S-shaped splines 121A, 121B and 121C. The flutes 120A, 120B and 120C form helical cutting edges 125A, 125B and 125C at the periphery of the shank 111. A transverse cross-section is shown of the cutting portion 112. The helical flutes 120A, 120B and 120C cooperate to form a web or core 126, which is essentially triangular. Areas of radial clearance or cutouts created by the flutes 121A, 121B and 121C outline the web or core. These areas of clearance are designated by numerals 130A, 130B and 130C. In transverse cross-section of the shank 111, splines 121A, 121B, and 121C of cutting flutes 120A, 120B, and 120C form teardrop-shaped clearance areas of variable depth. The cutting surfaces 125A, 125B, and 125C, or the perimeter of the shank, and the splines of the inner walls 121A, 121B, and 121C circumscribe clearance areas 130A, 130B, and 130C.

With further reference to FIG. 10E, it can be seen that walls 121A, 121B, and 121C intersect the periphery of the shank 111 at points 131A, 131B, and 131C. These intersections are equal distances apart or at 120° of separation forming a neutral cutting angle (90° angle to the tangent of the perimeter of shank 111) or slightly positive cutting angle (greater than 90° to the tangent of the perimeter of the shank 111). Lines drawn connecting point 131A, 131B, and 131C form an equilateral triangle. As shown in FIG. 10D, points 131A, 131B, and 131C intersect the periphery of the shank 111 alternately at 110°, 125°, and 125° of separation. Lines drawn connecting the point 131A, 131B, and 131C form an isosceles triangle. The outline of the triangle that is formed connecting point 131A, 131B, and 131C can vary. The outline may also be a scalene triangle with unequal sides. The difference in the number of degrees of separation between the longest spline and the short spline is not less than 60° and not greater than 150°.

The splines 121A, 121B, and 121C are S-shaped and are individually symmetrical. The bisector of each spline divides the spline equally into convex and a concave segments which form the S-shaped curve. The lines that bisect each spline can be drawn to the center of the core 126 and are equal in length. Further, an alternate bisector a can be drawn from the center of each spline through the greatest concavity the adjacent spline and perpendicular to the lines, which form the equilateral triangle. The bisectors a for each spline 121A, 121B, and 121C are equal.

The greatest depth of each spline can be defined by a segment of a. These depths can vary and, furthermore, be calculated as a percentage of the length of a. The greatest depths of splines 121A, 121C, and 121B, indicated with demarcated line segments 137A, 137B, and 137C, are 15%, 20%, and 25% of the length of a, respectively. The greatest convexities of splines 121A, 121B, and 121C are mirror images of the greatest concavities of the same splines. The depth and height of each spline can vary; however, the cross sectional diameter of the core portion 126 should generally not be narrower than approximately half or fifty percent of the cross sectional diameter of the shank of the instrument.

FIGS. 12A–12D illustrate another implementation, which is four sided or rectilinear in transverse cross-section and can be utilized to remove tissue and/or dentin from an ECS. The implementation shown includes a shank similar to the one described in FIGS. 10A–10E and a working portion 1212, which is tapered in a shank-to-tip direction. The tip 1213 can include a cutting surface, which is confluent the working surface 1212 (for example, like the tip shown in FIGS. 11A–11D). Alternatively, the leading tip 1213 (of the instrument shown in FIGS. 12A–12D) can include a non-cutting surface, which is confluent with the working surface 1212 (for example, like the tip shown in FIG. 9C). The MxFD 1217 is located near the shank end of the cutting surface and MnFD 1216 is located near the tip end of the cutting surface. The shank 1211 above the cutting surface 1212 is essentially cylindrical exhibiting a slightly smaller diameter than the cutting surface at the MxFD (also similar to the instrument described in FIGS. 10A–10E). The instrument can include a modified or rolled edge portion 1214, which can to be confluent with the cutting surface 1212. This rolled-edge feature is illustrated in FIGS. 9A–9D. A fitting, which is suitable for an engine driven motor with a handpiece and chuck or a handle utilized for manual instrumentation, is attached to the shank at its most proximal end (also similar to the fitting described in FIGS. 10A–10E).

With further reference to FIGS. 12A–12D, four continuous helical flutes 1220A, 1220B, 1220C, and 1220D are substantially concave grooves which follow the circumference of the working surface 1212 spiraling toward the leading tip 1213 forming concentric circles, which may be equidistant from each other or becoming increasingly tighter or more numerous as they approach the tip 1213. The total number of flutes from MxFD to the MnFD should be no fewer than 16 but not greater than 24. Helical flutes 1220A, 1220B, 1220C, and 1220D each originate at the MxFD at separate locations that are equally spaced apart around the circumference of the shank 1211 or more specifically at 90° of separation. Each flute is continuous along the length of the cutting surface 1212 to the leading tip 1213.

With reference to FIG. 12D, it can be seen that flutes 1220A, 1220B, 1220C, and 1220D have an S-shaped splines 1221A, 1221B, 1221C, and 1221D. The flutes 1220A, 1220B, 1220C, and 1220D form helical cutting edges 1225A, 1225B, 1225C, and 1225D at the periphery of the shank 1211. With reference to FIG. 12D, a transverse cross-section is shown of the cutting portion 1212. The helical flutes 1220A, 1220B, 1220C, and 1220D cooperate to form a web or core 1226, which is generally square-shaped. The web or core is outlined by areas of radial clearance or cut outs created by splines 1221A, 1221B, 1221C, and 1221D. These areas of clearance are designated by numerals 1230A, 1230B, 1230C and 1230D. In transverse cross-section of the shank, splines 1221A, 1221B, 1221C, and 1221D of cutting flutes 1220A, 1220B, 1220C, and 1220D form teardrop clearance areas of variable depth. Clearance areas 1230A, 1230B, 1230C, and 1230D are circumscribed by cutting edges 1225A, 1225B, 1225C, and 1225D, or the perimeter of the shank, and the splines of the inner walls 1221A, 1221B, 1221C, and 1221D.

With further reference to FIG. 12D, it can be seen that splines 1221A, 1221B, 1221C, and 1221D intersect the periphery of the shank 1211 at point 1231A, 1231B, 1231C, and 1231D, respectively. These intersections are equal distances apart or at 90° of separation, forming a neutral angles (90° angle to the tangent of the perimeter of shank 1211) or slightly positive cutting angles (greater than 90° to the tangent of the perimeter of the shank 1211). Lines drawn connecting point 1231A, 1231B, 1231C, and 1231D form a square.

The splines 1221A, 1221B, 1221C, and 1221D are S-shaped and are individually symmetrical. The bisector of each spline divides the spline equally into convex and a concave segments which form the S-shaped curve. The lines that bisect each spline can be drawn to the center of the core 1226 and are equal in length. Further, an alternate bisector a can be drawn from the center of each spline through the greatest concavity the opposite spline and is also equal in length.

The greatest depth of each spline can be defined by a segment of a. These depths can vary and, furthermore, be calculated as a percentage of the length of a. The greatest depths of splines 1221A and 1221C, indicated with demarcated line segments 1237A and 1237C, are 5% of the length of a. The greatest depth of splines 1221B and 1221D, indicated with line segments 1237B and 1237D, are 25% of a. The greatest convexities of splines 1221A, 1221B, 1221C, and 1221D are mirror images of the greatest concavities of the same splines. The depth and height of each spline can vary; however, the cross sectional diameter of the core portion 1226 should generally not be narrower than approximately half or fifty percent of the cross sectional diameter of the shank of the instrument.

FIGS. 13A–13E illustrate another implementation, which is four sided or rectagonal in transverse cross–section and can be utilized to remove tissue and/or dentin from an ECS.

The instrument includes a shank 311 similar to the one described above with respect to FIGS. 10A–10E and a working portion 312, which is tapered in a shank-to-tip direction. The tip 313 can include a cutting surface, which is confluent the working surface 312 (for example, like the tip shown in FIGS. 11A–11D). Alternatively, the tip 313 can display a non-cutting surface, which is confluent with the working portion 312 (for example, like the tip shown in FIG. 9C). The instrument includes an MxFD 317 and an MnFD 316. The shank 311 above the above the working portion 312 is essentially cylindrical exhibiting a slightly smaller diameter than the cutting surface at the MxFD. The shank here is similar to the one described in FIGS. 10A–10E. The instrument includes a modified or rolled edge portion 314, which is confluent with the cutting surface 312. This rolled-edge feature is illustrated in FIGS. 9A–9D. A fitting, which is suitable for an engine driven motor with a hand-piece and chuck or a handle utilized for manual instrumentation, is attached to the shank at its most proximal end also similar to the fitting described in FIGS. 10A–10E.

As shown in FIGS. 13A–13E, four continuous flutes 320A, 320B, 320C and 320D are substantially concave grooves, which follow the circumference of the working surface 312 spiraling toward the leading tip 313 forming concentric circles, which may be equidistant or become increasingly tighter or more numerous as they approach the tip. The total number of flutes from MxFD to the MnFD should be no fewer than 16 but not greater than 24. Flutes 320A, 320B, 320C, and 320D each originate at the MxFD at various locations spaced around the circumference of the shank, more specifically at 80°, 100°, 80°, and 100° of separation, respectively. Each flute is continuous along the length of the cutting surface 312 to the leading tip 313.

With reference to FIG. 13E, it can be seen that flutes 320A, 320B, 320C, and 320D have an S-shaped splines 321A, 321B, 321C, and 321D. The flutes 320A, 320B, 320C, and 320D form helical cutting edges 325A, 325B, 325C, and 325D at the periphery of the shank 311. As shown in FIG. 13E, a transverse cross-section is shown of the cutting portion 312. The flutes 320A, 320B, 320C, and 320D cooperate to form a web or core 326, which is essentially rectagonally shaped. The web or core is outlined by areas of radial clearance or cut outs created by the splines 321A, 321B, 321C, and 321D. These areas of clearance are designated by numerals 330A, 330B, 330C, and 330D. In transverse cross-section of the shank, the splines 321A, 321B, 321C, and 321D of flutes 320A, 320B, 320C, and 320D form teardrop clearance areas of variable depth. Clearance areas 330A, 330B, 330C, and 330D are circumscribed by cutting edges 325A, 325B, 325C, and 325D, or the perimeter of the shank, and the splines 321A, 321B, 321C, and 321D.

As shown in FIG. 13E, it can be seen that splines 321A, 321B, 321C, and 321D intersects the periphery of the shank 311 at points 331A, 331B, 331C, and 331D, respectively. These intersections are at 80°, 100°, 80°, and 100° of separation, respectively, forming neutral or slightly positive cutting angles. Lines drawn connecting point 331A, 331B, 331C, and 331D form a rectangle. The difference in degrees between the longest spline and the shortest spline is 20°. Alternatively, as shown in FIG. 13D, points 331A, 331B, 331C, and 331D can intersect the periphery of the shank at 90°, 95°, 80° and 95° of separation, respectively. Lines drawn connecting the point 331A, 331B, 331C, and 331D also form a rectangle. The outline of the trapezoid that is formed connecting point 331A, 331B, 331C, and 331D can vary. The difference in the number of degrees of separation between the longest spline and the short spline should not be less than 5° and not greater than 70°.

The splines 321A, 321B, 321C, and 321D are S-shaped and are individually symmetrical. The bisector of each spline divides the spline equally into convex and a concave segments which form the S-shaped curve. Alternate bisectors a and b can be drawn from the center of each spline through the greatest concavity the opposite spline.

The greatest depth of each spline can be defined segments of a and b. These depths can vary and, furthermore, be calculated as a percentage of the length of a and b. The greatest depths of splines 321A and 321C, indicated with demarcated line segments 337A and 337C, are 5% of the length of a. The greatest depth 321B and 321D, indicated with demarcated line segments 337B and 337D, are 5% of b. The greatest convexities of splines 321A, 321B, 321C, and 321D are mirror images of the greatest concavities of the same splines. The depth and height of each spline can vary; however, the cross sectional diameter of the core portion 326 should generally not be narrower than half or fifty percent of the cross sectional diameter of the shank of the instrument.

Alternatives

A number of implementations of the invention have been described. Nevertheless, it will be understood that various modifications may be made without departing from the spirit and scope of the invention. For example, in other implementations, similar instruments can include 5 or 6 flutes. The shanks and/or metal blanks from which these instruments can be fabricated and have slightly larger diameters providing enough material to facilitate the increased number of flutes. The flutes, therefore, would require fewer spirals per unit length. Instruments of increasing size, or diameter, become increasingly less flexible. Implementing more flutes and/or cutting the flutes deeper into the metal blanks during manufacture can facilitate compensation for the decrease in flexibility. In addition, wider and deeper spaces also provide greater opportunity to haul out debris from the apex to the coronal aspect of the tooth. Accordingly, other embodiments are within the scope of the following claims.

What is claimed is:

1. An endodontic instrument, comprising:
a shaft that includes an end, a tip, one or more flutes, and a longitudinal axis, wherein at least one flute includes a cutting edge that is the leading edge of the flute when the instrument is rotated in a first direction of rotation about the longitudinal axis so that the instrument is configured to cut, without requiring force to be applied to the instrument in an end-to-tip longitudinal direction, when the shaft is rotated in the first direction of rotation about the longitudinal axis, and wherein the at least one flute spirals around the shaft in the end-to-tip longitudinal direction and in a second direction of rotation that is opposite from the first direction of rotation.

2. The instrument of claim 1, further comprising:
at least one helix that includes one or more cross cuts.

3. The instrument of claim 1, wherein:
the shaft includes a portion where the cutting edge is rolled.

4. The instrument of claim 1, wherein:
the one or more flutes have S-shaped splines.

5. The instrument of claim 4, wherein:
the tip is a non-cutting tip.

6. The instrument of claim 4, wherein:
the tip is a cutting tip.

7. The instrument of claim 1, wherein:
the cutting edge of the flute has a zero cutting angle.
8. The instrument of claim 7, wherein:
a cross section of the shaft has a quadrilateral-like shape.
9. The instrument of claim 7, wherein:
a cross section of the shaft has a triangle-like shape.
10. The instrument of claim 1, wherein:
the shaft is fabricated from one of Ni—Ti and Ni—Ti alloy.
11. The instrument of claim 1, further comprising:
an attachment for coupling the shank end of the instrument to an engine operable to rotate the instrument.
12. The instrument of claim 1, wherein:
the cutting edge is a right handed cutting edge.
13. The instrument of claim 1, wherein:
the cutting edge is a left handed cutting edge.
14. The instrument of claim 1, wherein:
the instrument is a hand-type endodontic instrument.
15. The instrument of claim 1, wherein:
the instrument is a rotary-type endodontic instrument.
16. The instrument of claim 1, wherein:
the one or more flutes taper in a shank-to-tip direction.
17. The instrument of claim 1, wherein:
at least one flute has no radial lands.
18. The instrument of claim 1, wherein:
at least one flute has reduced radial lands.
19. An endodontic instrument, comprising:
a shaft that includes an end, a tip, one or more flutes, and a longitudinal axis, wherein at least one flute includes a cutting edge that is the leading edge of the flute when the instrument is rotated in a first direction of rotation about the longitudinal axis so that the instrument is configured to cut, without requiring the instrument to be threaded into a material to be cut, when the shaft is rotated in the first direction of rotation about the longitudinal axis, and wherein the at least one flute is situated to wrap around the shaft in an end-to-tip longitudinal direction and in a second direction of rotation that is opposite from the first direction of rotation.
20. An endodontic instrument, comprising:
a shaft that includes an end, a tip, one or more flutes, and a longitudinal axis, wherein the instrument is a rotary type instrument and at least one flute includes a cutting edge that is the leading edge of the flute when the instrument is rotated in a first direction of rotation about the longitudinal axis so that the instrument is configured to cut when the shaft is rotated in the first direction of rotation about the longitudinal axis, wherein the instrument is not required to be rotated in a reciprocating manner in order to cut, and wherein the at least one flute is situated to wrap around the shaft in an end-to-tip longitudinal direction and in a second direction of rotation that is opposite from the first direction of rotation.

* * * * *

UNITED STATES PATENT AND TRADEMARK OFFICE
CERTIFICATE OF CORRECTION

PATENT NO. : 7,094,056 B2
APPLICATION NO. : 10/764337
DATED : August 22, 2006
INVENTOR(S) : Michael J. Scianamblo It is certified that error appears in the above-identified patent and that said Letters Patent is hereby corrected as shown below:

On the Cover Page, Col. 2 (56) References Cited, Foreign Patent Documents; replace:
"WO02/0659398" with
--WO02/065938--

Signed and Sealed this

Twelfth Day of June, 2007

JON W. DUDAS
*Director of the United States Patent and Trademark Office*